US00PP25973P3

(12) United States Plant Patent
van Geest

(10) Patent No.: US PP25,973 P3
(45) Date of Patent: Oct. 6, 2015

(54) ***FICUS ELASTICA* PLANT NAMED 'NAIROBI'**

(50) Latin Name: *Ficus elastica*
Varietal Denomination: NAIROBI

(71) Applicant: Jan van Geest, 's-Gravenzande (NL)

(72) Inventor: Jan van Geest, 's-Gravenzande (NL)

(73) Assignee: J. van Geest Holding B.V. (NL)

( * ) Notice: Subject to any disclaimer, the term of this patent is extended or adjusted under 35 U.S.C. 154(b) by 190 days.

(21) Appl. No.: 13/998,425

(22) Filed: Oct. 30, 2013

(65) Prior Publication Data

US 2015/0121580 P1 Apr. 30, 2015

(51) Int. Cl.
*A01H 5/12* (2006.01)

(52) U.S. Cl.
USPC ..... Plt./211

(58) Field of Classification Search
USPC ..... Plt./211
See application file for complete search history.

*Primary Examiner* — Anne Grunberg
(74) *Attorney, Agent, or Firm* — Cassandra Bright

(57) ABSTRACT

A new and distinct *Ficus elastica* cultivar named 'NAIROBI' is disclosed, characterized by, a compact shape and elliptic to ovate green to grey-green leaves. The new variety is a *Ficus elastica* typically produced as an ornamental plant.

1 Drawing Sheet

Latin name of the genus and species: *Ficus elastica.*
Variety denomination: 'NAIROBI'.

BACKGROUND OF THE INVENTION

The new cultivar is the product of chance discovery. The new variety originated as a naturally occurring whole plant mutation of *Ficus elastica* 'Melany' U.S. Plant Pat. No. 9,923. *Ficus* 'NAIROBI' is the same variety described in EU application number 2009/2418, grant EU 30778. The new variety was first available publicly December 2012. Until this time, plants of the new variety were either directly under the control of the inventor, or subject to confidential testing by the CPVO during the application process.

The new variety was discovered by the inventor, Jan van Geest, a citizen of Netherlands, during Autumn of 2007 in a commercial greenhouse belonging to the inventor in s'Gravenzande, the Netherlands. After identifying the new variety as a potentially interesting selection, the inventor continued confidential testing and propagation of 'NAIROBI', assessing stability of the unique characteristics of this variety.

Asexual reproduction of the new cultivar 'NAIROBI' was first performed at a greenhouse in s'Gravenzande, the Netherlands, by vegetative cuttings in August of 2008. Access to all plants was restricted, as plants were kept in locations that are not open to the public. Through subsequent propagation multiple generations have been reproduced, which have shown that the unique features of this cultivar are stable and reproduced true to type.

SUMMARY OF THE INVENTION

The cultivar 'NAIROBI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NAIROBI.'

These characteristics in combination distinguish 'NAIROBI' as a new and distinct *Ficus elastica* cultivar:

1. Compact plant shape.
2. Ovate to elliptic leaves.
3. Green to greyed-green mature leaves.

PARENT COMPARISON

Plants of the new cultivar 'NAIROBI' are similar to the parent, *Ficus elastica* 'Melany' in most horticultural characteristics. However the new variety, 'NAIROBI' differs from 'Melany' in the following characteristics:

1. More compact in plant form than parent.
2. Smaller foliage than parent variety.

COMMERCIAL COMPARISON

Plants of the new cultivar 'NAIROBI' can be compared to the commercial variety *Ficus elastica* 'Mini Melany', unpatented. However the new variety, 'NAIROBI' differs from 'Mini Melany' in the following characteristics:

1. More compact in plant form than 'Mini Melany'.
2. Stronger growth and easier to growth than 'Mini Melany'.

BRIEF DESCRIPTION OF THE PHOTOGRAPH

The accompanying photograph in FIG. 1 illustrates in full color a typical plant of 'NAIROBI' grown in a commercial greenhouse in s'Gravenzande, the Netherlands. This plant is approximately 7 weeks old, shown planted in a 14 cm pot, with 3 cuttings per pot.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'NAIROBI' plants grown in a greenhouse in s'Gravenzande, the Netherlands. The plant described is approximately 6 weeks old, grown in a 14 cm pot, with 3 cuttings in the pot. Temperatures ranged from 20° C. at night to 25° C. during the day. No artificial light, photoperiodic treatments were given to the plants. No chemical treatments were given to plants. Measurements and numerical values represent averages of typical plant types.

Botanical classification: *Ficus elastica* 'NAIROBI'.

PROPAGATION

Typical propagation method: Vegetative cuttings.

Time to initiate rooting: About 5 weeks at approximately 25° C.

Time to produce a rooted plantlet: 6 weeks.

Root description: Roots fine, moderately branched, non-fibrous, not-fleshy colored greyed-yellow; near RHS 162A and 162B.

PLANT

Growth habit: Broad upright.

Age of plant described: 7 weeks.

Container size: 14 cm circular container (three plants per pot).

Height: Measured from top soil line of pot, approximately 23.8 cm.

Plant spread: Approximately 16.1 cm.

Growth rate: Moderate.

Branching characteristics: Moderately to freely branching, basal branching.

Primary lateral branches:

*Length*.—Approximately 14.6 cm.
*Diameter*.—Approximately 0.5 cm.
*Texture*.—Glabrous, slightly glossy.
*Color*.—Green; near RHS 143A, flushed greyed-green at the nodes; near RHS 197A.
*Strength*.—Strong.
*Internode length*.—Average 0.9 cm.
*Adventitious roots at nodes*.—Non present.

Secondary lateral branches:

*Length*.—Approximately 7.2 cm.
*Diameter*.—Approximately 0.4 cm.
*Texture*.—Glabrous, slightly glossy.
*Color*.—Green; near RHS 143A.
*Strength*.—Strong.
*Internode length*.—Approximately 1.7 cm.
*Adventitious roots at nodes*.—Non present.

New shoot growth characteristics:

*Color*.—Greyed-red; near RHS 180C and 180D.
*Texture*.—Glabrous, moderately glossy.

FOLIAGE

Leaf:

*Arrangement*.—Alternate, single.
*Average quantity per lateral branch*.—Average: 17.
*Average length*.—Approximately 10.8 cm.
*Average width*.—Approximately 4.2 cm.
*Shape of blade*.—Ovate to elliptic, slightly carinate.
*Apex*.—Short apiculate.
*Base*.—Attenuate.
*Margin*.—Entire.
*Texture of top surface*.—Glabrous, very glossy.
*Texture of bottom surface*.—Glabrous, slightly glossy.
*Aspect*.—Leaves in an average angle of 30° to lateral branch (=0°).
*Color*.—Young foliage upper side: Grey-brown; near RHS N199B but darker. Young foliage under side: Grey-brown; in between RHS N199A and N199B. Mature foliage upper side: Green to greyed-green; in between RHS 139A and N189A but darker. Mature foliage under side: Yellow-green to brown; in between near RHS 147A and N200B but darker.
*Venation*.—Type: Pinnate. Venation color upper side: Yellow-green to grey-brown; in between RHS 152A and 199A. Venation color under side: Greyed-purple; near RHS 183B and 183C.

FLOWER

Flowering not observed.

OTHER CHARACTERISTICS

Seeds and fruits: No seeds/fruits observed.

Disease/pest resistance: Neither resistance not susceptibility to the normal diseases and pests of *Ficus elastica*.

Temperature tolerance: No tolerance for cold temperatures. Can tolerate warm temperatures to at least 40° C.

What is claimed is:

1. A new and distinct cultivar of *Ficus elastica* plant named 'NAIROBI' as herein illustrated and described.

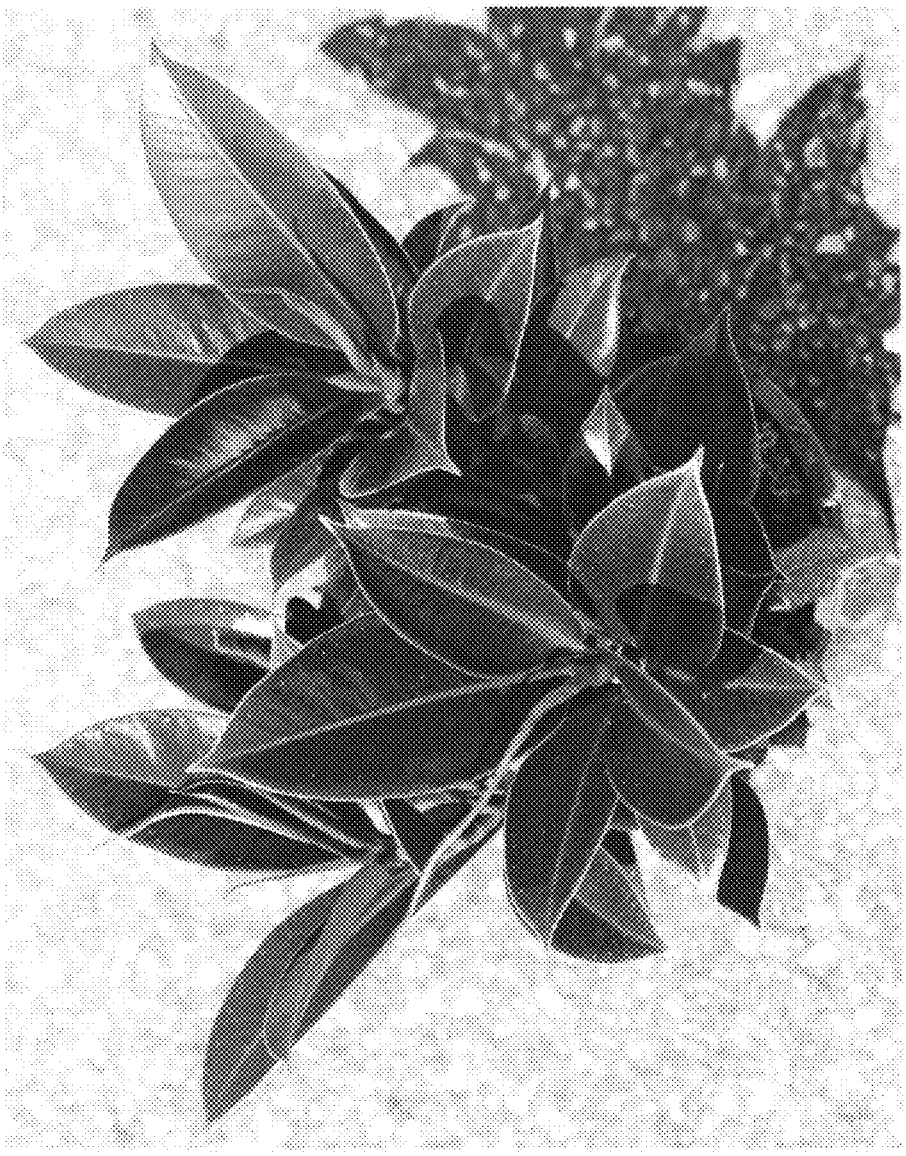

* * * * *